United States Patent [19]

Vosika et al.

[11] Patent Number: 5,750,665
[45] Date of Patent: May 12, 1998

[54] PREPARATION OF GLUCOSAMINYL MURAMIC ACID DERIVATIVES

[76] Inventors: Gerald J. Vosika, 3505 S. Riverview Cir.; Fanfeng Ma, 2930 Village Green Dr., both of Moorhead, Minn. 56560

[21] Appl. No.: 539,292

[22] Filed: Oct. 4, 1995

[51] Int. Cl.⁶ ............................................. C07H 5/00
[52] U.S. Cl. ................................ 536/17.2; 536/18.5
[58] Field of Search ........................... 536/4.1, 17.2, 536/17.7, 18.5, 18.6, 124

[56] References Cited

U.S. PATENT DOCUMENTS

| | | | |
|---|---|---|---|
| 4,391,800 | 7/1983 | Durette et al. | 514/18 |
| 4,395,399 | 7/1983 | Ovchinnikov et al. | 424/279.1 |
| 4,545,932 | 10/1985 | Takase et al. | 530/322 |
| 4,774,231 | 9/1988 | Petitou et al. | 514/53 |
| 4,950,645 | 8/1990 | Vosika et al. | 424/279.1 |
| 5,371,022 | 12/1994 | Hasegawa | 536/17.5 |

FOREIGN PATENT DOCUMENTS

| | | |
|---|---|---|
| 250284 | 5/1988 | Czechoslovakia . |
| 578112 | 1/1994 | European Pat. Off. . |

OTHER PUBLICATIONS

Kusumoto, et al., *Bull. Chem. Soc. Jpn.* 59, 1411–1417 (1986).
Termin, et al., *Liebigs Ann. Chem.* 527–533 (1992).
Baker, et al., *J. Org. Chem.*, 19: 1786–1792, (Jun. 1954).
Bomford, et al., *Aids Research and Human Retroviruses*, 8: 1765–1771, (1992).
Durette, et al., *Carbohydrate Research*, 77: C1–C4, ( Aug. 1979).
Chapleur, et al., *J. Chem. Soc. Perkin Trans.*, 1: 703–705, (1989).
Durette, et al., *Tetrahedron Lett.*, 42: 4013–4016 (Apr. 1979).
Farkas, et al., *Carbohydrate Research*, 163: 63–72, (1987).
Flowers, et al., *J. Org. Chem.*, 28: 2983–2986 (Nov. 1963).
Furuta, et al., *Agric. Biol. Chem.*, 50 (10): 2561–2572 (Apr. 1986).
Gross, et al., *Liebigs Ann. Chem.*, 37–45, (May 1986).
Guinand, et al., *Eur. J. Biochem.*, 143: 359–362 (Feb. 1984).
Kanie, et al., *J. Am. Chem. Soc.*, 116: 12073–12074 (Sep. 1994).
Kantoci, et al., *Carbohydrate Research*, 162: 227–235 (1987).
Kawata, et al., *Agric. Biol. Chem.*, 48: 1783–1793 (1984).

Keglevic, et al., *Biochimica et Biophysica Acta*, 585: 273–281 (1979).
Keglevic, et al., *Croatica Chemica Acta*, 58: 569–581, (1985).
Kiso, et al., *Carbohydrate Research*, 104: 253–269 (Jan. 1982).
Kusumoto, et al., *Bull. Chem. Soc. Jpn.*, 59:1419–1423 (Jan. 1986).
Kusumoto, et al., *Tetrahedron Letters*, 45: 4407–4410 (Aug. 1978).
Ledvina, et al., *Collect. Czech. Chem. Commun.*, 54: 2784–2794 (Mar. 1989).
Ledvina, et al., *Carbohydrate Research*, 251: 269–284 (1994).
Merser, et al., *Tetrahedron Letters*, 13: 1029–1032 (1973).
Mukaiyama, et al., *Chem. Lett.*, 431–432 (1981).
Nicolaou, et al., *J. Am. Chem. Soc.*, 105: 2430–2434 (1983).
Nicolaou, et al., *J. Am. Chem. Soc.*, 106: 4189–4192 (Mar. 1984).
Nicolaou, et al., *J. Am. Chem. Soc.*, 107: 5556–5558 (Apr. 1985).
Nicolaou, et al., *J. Am. Chem. Soc.*, 12: 3693–3695 (1990).
Pozsgay, et al., *J. Org. Chem.*, 52: 4636–4637 (1987).
Pozsgay, et la., *Tetrahedron Letters*, 28, No. 13, 1375–1376 (Jan. 1987).
Pozsgay, et al., *Carbohydrate Research*, 179: 61–75 (1988).
Sava, et al., *Cancer Immunol. Immunother*, 15: 84–86 (1983).
Termin, et al., *Liebigs Ann. Chem.*, 789–795 (1989).
Vosika, et al., *J. of Immunotherapy*, 10: 256–266 (Feb. 1991).
Campbell, et al. *J. of Immunology*, 145: 1029–1036 (Aug. 1990).

*Primary Examiner*—Elli Peselev

[57] ABSTRACT

The present invention provides a method for the preparation of disaccharides, such as glucosaminyl muramic acids peptides and derivatives. The method includes condensing a protected muramic acid ester with a 1-organothio- or 1-fluoroglucosamine derivative in the presence of a suitable promoter to produce a protected glucosaminyl muramic acid ester. The protected glucosaminyl muramic acid ester may be used to prepare disaccharide peptides, such as N-acetylglucosaminyl-N-acetylmuramyl dipeptides, which have demonstrated immunological activity. Protected muramic acid esters and 1-organothio- or 1-fluoro- glucosamine compounds which may be employed as intermediates in the method are also provided.

10 Claims, No Drawings

PREPARATION OF GLUCOSAMINYL MURAMIC ACID DERIVATIVES

BACKGROUND OF THE INVENTION

Intact microbial agents are known to have immunomodulatory activity as demonstrated by anti-infectious activity, anti-cancer activity, and adjuvant activity. This activity is evidenced by an increase in both humoral and cellular immune response. The active components of these microbial agents, as found, for example, in microbial agents of the class mycobacteriaceae, nocardia, and micrococcus, consist of the peptidoglycan cell wall skeleton and more particularly the repeating N-acetylglucosaminyl-N-acetylmuramyl peptide units. From this peptidoglycan, N-acetylmuramyl-L-alanine-D-isoglutamine, also known as muramyl dipeptide (MDP), has been identified as the minimal unit possessing immunological activities.

A large number of MDP derivatives have been synthesized and shown to possess immunological activity. While the monosaccharide muramyl dipeptides are immunilogically active, studies have established that the disaccharide dipeptide, which corresponds to the basic repeating unit of the cell wall peptidoglycan, possesses greater immunomodulating activity. This is shown, for example, by the anti-cancer activity of the monomeric units when given intravenously to mice bearing the Lewis lung carcinoma or the MCA mammary carcinoma (see, e.g., Sava et al., *Cancer Immunology Immunotherapy*, 15, 84–86 (1983)). Similarly, in humans, immunotherapy utilizing a disaccharide peptide derivative, such as N-acetylglucosaminyl-N-acetylmuramyl-L-Ala-D-isoGlu-L-Ala-glyceroldipalmitoyl, has been more effective than a related monosaccharide peptide derivative, such as N-acetylmuramyl-L-Ala-D-isoGlu-L-Ala-phosphatidylethanolamine (see, e.g., Vosika et al., *Journal of Immunotherapy*, 10, 256–266 (1991)). Disaccharide peptides have also demonstrated enhanced efficacy in vaccine preparations.

The general use of the disaccharide peptide and related analogues has, however, been hampered by the cost of production. Typically, either the disaccharide dipeptide or the basic disaccharide itself (N-acetylglucosaminyl-N-acetylmuramic acid) is isolated from the cell walls of micrococcus lysodysticus through a process of cell fractionation, delipidation, enzymatic digestion, and extensive column chromatography. Alternative methods for isolation of the disaccharide and/or disaccharide dipeptide from biomass have included purification from the peptidoglycan complex excreted in penicillin treated cultures of a Brevibacterium *Diverticulum mutant*, enzymatic preparation from peptidoglycan of Actinomadura R39, and enzymatic preparation from hydrolysate of *L. plantanum* cell wall. The yields from such biologically based procedures are typically extremely low, on the order of 2% or less.

A variety of routes for the preparation of disaccharide structures by chemical synthesis have been reported as well. While a number of the reported routes have been successful in producing a disaccharide, the chemical synthetic methods have typically been characterized by low yields, large numbers of steps, difficult to handle reagents, stringent requirements on reaction conditions and/or lack of flexibility with regard to starting materials and products.

For example, methods of preparing disaccharides based on the condensation of a N-protected glucosaminyl donor with the hydroxyl group of glycosyl acceptor have been disclosed. The reported methods include condensations of N-protected glucosaminyl donors having a variety of leaving and/or activating groups (e.g., bromo, chloro, fluoro, methylthio, phenylthio, oxazoline, and trichloroacetimidate) with a glycosyl acceptor. Reports of condensations employing an N-protected 4-hydroxymuramic acid ester derivative as the acceptor have been extremely rare, however, perhaps because of the increased steric hindrance provided by the lactyl ether group. In order to avoid this problem, synthetic routes to protected glucosaminyl muramic acid ester compounds have typically delayed the introduction of the lactyl group until after the glycosylation step.

The condensation of an N-protected glucosaminyl chloride donor with an N-protected 4-hydroxymuramic acid ester acceptor has been dislcosed. The condensation, however, is carried out in the presence of at least a full equivalent of silver triflate and must be run under a very specific set of reaction conditions which include the absence of base.

There is, accordingly, a continuing need for improved processes for the production of disaccharide dipeptide compounds via a chemical synthesis which includes the direct glycosylation of an N-protected 4-hydroxymuramic acid ester derivative.

SUMMARY OF THE INVENTION

The present invention is directed to a method for the preparation of disaccharide compounds, such as glucosaminyl muramic acid esters and related peptide derivatives. The present method may be utilized to produce protected 2-amino-2-deoxy-β-O-glucopyranosyl-(1→4)-muramic acid esters and related disaccharide peptides, such as N-acetylglucosaminyl-N-acetylmuramyl dipeptides, N-acylglucosaminyl-N-acylmuramyl dipeptides and related disaccharide peptide derivatives are known to have immunomodulating activity (e.g., immunoaugmenting activity).

The method includes condensing a protected glucosamine compound in the presence of a suitable promoter with a muramic acid ester derivative to form a protected glucosaminyl muramic acid ester derivative. In a preferred embodiment, the method includes condensing a muramic acid ester derivative with a protected 1-organothio- or 1-fluoroglucosamine compound to produce a 2-amino-2-deoxy-β-O-glucopyranosyl-(1→4)-muramic acid ester derivative.

The present invention is also directed to a muramic acid ester derivative having the formula:

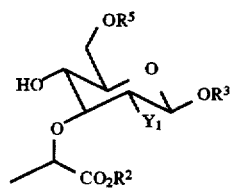

wherein $R^2$ is a benzyl or substituted benzyl group, $R^3$ and $R^5$ are hydroxyl protecting groups and $Y_1$ is a protected amino group.

Another embodiment of the invention provides a glucosaminyl muramic acid ester derivative having the formula:

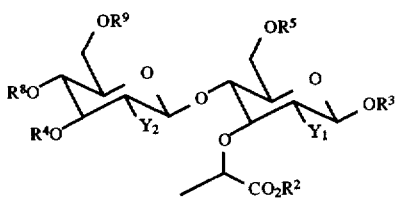

wherein $R^2$ is benzyl or substituted benzyl; $R^3$, $R^4$, $R^5$, $R^8$, and $R^9$ are hydroxyl protecting groups; and $Y_1$ and $Y_2$ represent protected forms of an amino group.

The glucosaminyl muramic acid ester derivatives synthesized by the present method can be easily converted into biologically active disaccharide peptides and peptide derivatives. For example, the method may be utilized in the preparation of peptides and peptide derivatives, such as derivatives of the known compound muramyldipeptide (MDP). Muramyldipeptides (MDP) and related disaccharide peptides have a demonstrated effect in altering and augmenting immunity in the treatment of a variety of conditions in humans. In addition, disaccharide dipeptides and related derivatives are nontoxic when administered at biologically active human dosages.

The present method of preparing glucosaminyl muramic acid derivatives has the advantages of relative ease and low expense when compared to known synthetic methods, whether based on fermentation/isolation procedures or on a chemical synthesis. In addition to the relatively low cost and ease of synthesis, the present method for preparing disaccharide derivatives has the potential to be run on a large-scale and to form the basis for commercially useful synthetic chemical production process for disaccharides.

DETAILED DESCRIPTION OF THE INVENTION

The method of the present invention provides a synthesis of glucosaminyl muramic acid derivatives, such as a 2-amino-2-deoxy-β-O-glucopyranosyl-(1→4)-muramic acid derivative (Compound I). The method includes the condensation of a donor, such as a protected glucosamine (Compound II) with an acceptor, such as a protected muramic acid ester derivative (Compound III). (See e.g., Scheme I below). The condensation is typically carried out in the presence of a suitable promoter. The promoter serves to activate the anomeric substituent of the protected glucosamine donor and increase its efficacy as a leaving group.

A variety of compounds may be employed as starting materials for the present condensation reaction. The protected glucosamine and the muramic acid ester derivative may include any of a number of different protecting groups attached to the hydroxyl and amino moieties. Suitable protecting groups include any group capable of protecting the moiety to which it is attached during the condensation reaction and which may be readily removed thereafter. In a preferred embodiment, the protecting groups facilitate the selective deprotection of the various hydroxyl or amino groups in the disaccharide condensation product. In another preferred embodiment, the protecting groups are chosen such that the muramic acid ester group may be selectively converted into the corresponding acid without cleavage of any of the hydroxyl or amino protecting groups. In yet another embodiment, all of the hydroxyl protecting groups are removed in addition to the muramic ester group to generate an N-acylated glucosaminyl muramic acid, such as N-acetylglucosaminyl-N-acetylmuramic acid.

The hydroxyl moieties on the protected glucosamine and muramic acid ester derivative may be protected with any of a variety standard groups capable of protecting the hydroxyl group during the condensation reaction. Suitable hydroxyl protecting groups include alkyl, substituted alkyl, alkanoyl, benzoyl, substituted benzoyl radicals, benzyl, substituted benzyl, and other araalkyl groups which include a —C—Ar subunit (e.g., $Ph_2CH$— or $Ph_3C$—). Typically, the hydroxyl moieties are protected with an acyl group (e.g., acetyl) or a benzyl group. In addition to being stable under the conditions commonly employed for the condensation reaction, such hydroxyl protecting groups are typically readily cleaved to expose the hydroxyl groups of the disaccharide condensation product. In a preferred embodiment of the reaction, the hydroxyl moieties on the protected glucosamine donor (Compound II) are protected with an acyl group, a benzyl group or a substituted benzyl group and, more preferably, with an acetyl group or a benzyl group.

The amino groups of the glucosamine compound (Compound II) and muramic acid ester derivative (Compound III) are typically protected as part of a group which includes an N—C(O)— subunit. Suitable examples of such protected forms of an amino group include acylated amines, carbamylated amines and imido groups. Among the protected forms of an amino group which are suitable for use in the present invention are acylated amines, $(NHC(O)R^6)$ or carbamylated amines $(NHC(O)OR^7)$, wherein $R^6$ is C(1–6) alkyl, substituted C(1–6)alkyl, benzyl, substituted benzyl, phenyl or substituted phenyl; and $R^7$ is C(1–6)alkyl, substituted C(1–6)alkyl, benzyl, or substituted benzyl. The amino groups may also be protected in the form of an imido group. Examples of suitable imido groups include phthalimido, maleimido or succinimido groups. The use of an imido group, such as a phthalimido group, to protect the 2-amino group of a glucosamine donor can exert a strong 1,2-trans directing effect which is useful in creating the desired β-anomer of the disaccharide condensation product.

As employed herein, the term "substituted alkyl" refers to an alkyl group substituted with one or more substituents. Examples of suitable substituents which may be present on the alkyl group include C(1–3)alkoxy, C(1–3) organothio, C(2–4)carboalkoxy (—C(O)OR), a hydroxyl functionality modified by esterification with a C(1–4) carboxylic acid ("acyloxy"; —OC(O)R), and trialkylsilyl.

The terms "substituted benzyl" or "substituted phenyl" employed herein refer to a benzyl group or a phenyl group in which the phenyl ring is substituted by one or more substituents. Examples of suitable phenyl ring substituents include nitro, halogen (e.g., chloro- or bromo-), C(1–3)alkyl, C(1–3)alkoxy, carboalkoxy (—C(O)OR'), and acyloxy (—OC(O)R'), wherein R' is a C(1–3) alkyl group.

The term "substituted acyl" refers to a —C(O)R" group wherein the R" is a substituted alkyl, substituted benzyl or substituted phenyl (as defined herein). Examples of suitable substituted acyl groups include perhalogenated aliphatic acyl groups (e.g., perfluorinated or perchlorinated acyl groups) and benzoyl groups substituted by one or more subsitutents such as halogen, C(1–3)alkyl, or C(1–3)alkoxy.

Compound II is a glucosamine derivative having a protecting group attached to the nitrogen at the 2-position of the glucosamine structure ("$Y_2$"). The protecting group typically includes the nitrogen atom in the form of an NHC(O) $R^6$, $NHC(O)OR^7$, or imido group. Preferably, the amino group of Compound II is protect as part of an imido group such as a phthalimido, maleimido or succinimido group. Protection of the 2-amino group of the glucosamine structure as an imido protecting group is desirable because it hinders the production of the α-anomer in a condensation reaction. Imido groups, such as the phthalimido group, are known to have a strong 1,2-trans directing effect which is useful in creating the desired β-anomer. Depending on the desired product, however, it may be advantageous to protect the 2-amino group in the form of an N-acyl group. More preferably, the $Y_2$ group at the 2-position of Compound II is a phthalimido group or an N-acetyl group.

In addition, Compound II typically has protecting groups attached to the hydroxyl moieties at the 2, 3, and 6 positions ($R^4$, $R^8$, and $R^9$). Preferably, the protecting group attached to these hydroxyl moieties is benzyl or acetyl.

Finally, Compound II includes a functional group at the 1 position which is capable of being displaced ("leaving group") during the condensation reaction which forms an oxygen bridge between the 1-position of the glucosaminyl ring (Compound II) and the 4-position of the muramyl ring (Compound III). The leaving group ("X") is a fluorine or an organothio group. Glucosamine derivatives having the formula of Compound II, while relatively stable, are capable of being condensed with the sterically hindered 4-hydroxy group of a muramic acid ester compound. Suitable organothio groups include —$SR^1$ where the $R^1$ is C(1-6)alkyl, phenyl or substituted phenyl. Preferably the organothio group is a thiomethyl group (—SMe) or a thiophenyl group (—SPh).

Compound II may be prepared from commercially available materials by adding the appropriate protecting groups using methods known to those skilled in the art. The organothio- forms of Compound II may be prepared by reaction of a corresponding O-glycoside, such as 2-deoxy-2-phthalimido-1,3,4,6-tetra-O-acetyl-β-D-glucopyranose, with an alkylthio- or arylthio- trimethylsilyl sulfide (TMSSR$^1$) in the presence of a catalyst such as trimethylsilyl triflate or boron trifluoride etherate. Alternatively, the organothio- forms of Compound II may be prepared by the Lewis acid catalyzed reaction of a suitably protected β-D-glucopyranose with a thioalcohol ($R^1$SH). (See, e.g., Nicolaou et al., *J. Am. Chem. Soc.*, 105, 2430 (1983) and 112: 3693, 1990; and Pozsgay et al., *Tetrahedron Lett.* 28, 1375 (1987) and *Carbohydr. Res.*, 179, 61 (1988)). The fluoroform of Compound II can be prepared by reaction of the organothio- form of Compound II with N-bromosuccinimide and diethylaminosulfur trifluoride ("DAST").

Compound III is a muramic acid ester derivative having a protected amino group at the 2-position ($Y_1$) and an unprotected hydroxyl moiety at the 4-position. The protected amino group is typically in the form of an N-acyl group, such as N-acetyl group. The amino group may, however, also be protected using other standard amino protecting groups such as an imido group or a carbamate group. In a preferred embodiment of the invention $Y_1$ is an acetyl group, as N-acetyl muramic acid esters may serve as precursors for N-acetyl disaccharides known to have immunomodulating activity.

In addition, Compound III typically has protecting groups ($R^3$ and $R^5$) attached to the hydroxyl moieties at positions 1 and 6. The $R^3$ and $R^5$ groups are typically each independently an acyl group, a benzyl group or a substituted benzyl. Preferably, the protecting group attached to the hydroxyl moiety at position 1 is benzyl and the protecting group attached to the hydroxyl moiety at position 6 is benzyl or substituted benzyl. Alternatively, either of $R^3$ or $R^5$ may be an N-acetyl group. More preferably, $R^3$ and $R^5$ are independently N-acetyl or unsubstituted benzyl.

The carboxylic acid moiety on the muramic acid ester derivative in present in the form of an ester group. The carboxylic acid moiety may be esterified with an alkyl, substituted alkyl, araalkyl, or substituted araalkyl group. Preferably, the carboxyl protecting group is esterfied with a C(1-6) alkyl, benzyl or substituted benzyl group. More preferably, carboxylic acid moiety is present as a methyl or benzyl ester. Depending on the choice of other protecting groups, the methyl ester often permits the selective hydrolysis of the ester group without cleavage of the hydroxyl protecting groups, e.g., under basic conditions or by treatment with a nucleophilic reagent such as lithium iodide (LiI). The benzyl ester is quite stable and is less prone to lactonization than simple alkyl esters (e.g., a methyl ester). In addition, the benzyl ester may be very cleanly cleaved in high yield to provide the corresponding muramic acid derivative. For example, the benzyl ester group may be cleaved under reducing conditions, such as by hydrogenolysis in the presence of a transition metal catalyst and a hydrogen source (e.g., cyclohexene or ammonium formate). As with the methyl ester, appropriate choice of the other protecting groups present (e.g., protection of the hydroxyl groups with an acetyl group) may permit the selective cleavage of the benzyl ester without removal of the hydroxyl protecting groups. Even where the hydroxyl groups are protected as benzyl esters, it may be possible to selectively cleave the benzyl ester without deprotecting the hydroxyl groups. For example, a glucosaminyl muramic acid ester such as Compound IV below where $R^2$, $R^3$ and $R^5$ are all benzyl may be selectively deesterified by treatment cyclohexene in the presence of a palladium catalyst such as palladium hydroxide (Pd(OH)$_2$).

Compound III can be obtained from a protected muramic acid derivative by a variety known methods. For example, the acetal ring of a compound such N-acetyl-4,6-O-benzylidene muramic acid may be selectively cleaved by treatment with sodium cyanoborohydride and 1N hydrogen chloride-diethyl ether in tetrahydrofuran (THF) to liberate the hydroxyl group at position 4 of the muramyl ester. (See e.g., Chaplerer et al., *J. Chem. Soc. Perkin Trans.*, 1, 703 (1989); and Keglevic et al., *Croatica Chem Acta*, 58, 569 (1985)). N-acetyl-4,6-O-benzylidene muramic acid is commercially available (e.g., from Sigma Chemical Company, St. Louis, Mo.) or may be produced by known methods (see, e.g., Flowers et el., *J. Org. Chem.*, 28, 2983 (1963); and Gross et al., *Liebigs Ann. Chem.*, 37 (1986)). The anomeric hydroxyl group at the 1-position of muramic acid may be protected using a variety of known methods. Similarly, the carboxylic acid group may be esterified, either before or after the introduction of the other protecting groups onto the muramic acid framework, using a number of methods well known to those skilled in the art.

The condensation reaction between Compound II and Compound III to form a 2-amino-2-deoxy-β-O-glucopyranosyl-(1→4)-muramic acid ester derivative (Compound I) is typically carried out under mild conditions in the presence of a suitable promotor. The promoter can be any substance which activates the leaving group at the 1-position of the glucosamine derivative (Compound II) without substantially reacting with the protected hydroxyl, amino, and carboxyl groups of either of the starting materials (Compounds II and III) or the product (Compound I). The promoter typically includes a thio-activator, such as nitrosonium tetrafluoroborate, an alkyl sulfenyl triflate, or an N-halosuccinimide, or a fluorophilic reagent, such as a silver(I) salt or tin(IV) fluoride (SnF$_4$).

Suitable promoters for condensation reactions involving the organothio- form of Compound II include nitrosonium tetrafluoroborate, an alkyl sulfenyl triflate, or an N-halosuccinimide, such as N-bromosuccinimide or N-iodosuccinimide. The condensation using the N-halosuccinimide may be carried out in the presence of silver triflate (AgOTf) or triflic acid (HOTf). Condensations involving an organothio- glucosamine donor are typically carried out in the presence of the N-halosuccinimide and a catalytic amount (based on the amount of glucosamine donor) of silver triflate. Preferably, the promoter includes the N-halosuccinimide and 1–30 mole % (based on the amount of glucosamine donor) and, more preferably, 5–15 mole % silver triflate. Condensation reactions involving the methylthio- form of Compound II preferably are carried out in the presence of a promoter which includes nitrosonium tetrafluoroborate. A preferred promoter for condensation reactions involving the phenylthio- form of Compound II includes N-bromosuccinimide and silver triflate.

Suitable promoters for the present condensation reaction involving the fluoro- form of Compound II include a Lewis acid catalyst, such as $SnCl_2$, $Cp_2ZrCl_2$ or $Cp_2HfCl_2$, and a silver(I) salt, such as $AgClO_4$, $AgBF_4$ or AgOTf. In addition to the soft acid, the promoter used with the fluoro- form of Compound II typically includes from about 1.2 to about 2.0 and, preferably, from about 1.3 to about 1.5 equivalents of the silver(I) salt per equivalent of the glucosaminyl fluoride donor. Another example of a suitable reagent which may be employed as a promoter in the present method is tin(IV) fluoride ($SnF_4$). Preferably, the promoter used for condensations involving the fluoro- form of Compound II includes $SnCl_2$ and $AgClO_4$.

The coupling reaction is typically carried out in an aprotic organic solvent having good solvating power. Suitable organic solvents include organochlorine compounds, such as dichloromethane ($CH_2Cl_2$) and 1,2-dichloroethane ($CH_2ClCH_2Cl$) and aromatic solvents (e.g., toluene). $CH_2Cl_2$ is preferably included as part of the solvent used to dissolve the components of a typical reaction mixture.

In a preferred embodiment of the invention, the condensation reaction is carried out under substantially anyhydrous conditions. For example, the reaction(s) may be run under an atmosphere of an inert gas (e.g., nitrogen or argon) using predried reagents and starting materials. An efficient drying agent such as powdered 4A molecular sieves may be added to the reaction mixture. The molecular sieves efficiently remove traces of water from the solvent and reagents, thereby enhancing the yield and efficiency of the coupling reaction.

Disaccharide peptides having immunological modifying activity may be prepared from Compound I by (i) cleaving off the $R^2$ group of the glucosaminyl muramic acid ester derivative and (ii) coupling the resulting glucosaminyl muramic acid with the N-terminal α-amino group of an amino acid or peptide ("Pep nucleophile") to produce a glucosaminylmuramyl peptide derivative ("GM-Pep compound"). The Pep nucleophile and the resulting GM-Pep compound typically include more than one amino acid residue, e.g., a dipeptide, tripeptide or a protected derivative thereof. For example, a glucosaminyl muramic acid derivative (e.g., a protected N-acetylglucosaminyl-N-acetylmuramic acid) may be coupled with the N-terminal α-amino group of an ester of L-alanyl-D-isoglutamine to form a glucosaminylmuramyl dipeptide derivative.

The protecting groups of Compound I can be cleaved by methods known to those skilled in the art (see for example the methods described in "Protecting Groups in Organic Synthesis," Greene, ed., John Wiley & Sons, New York, N.Y.). The coupling reaction between the glucosaminylmuramic acid derivative and the Pep nucleophile may be carried out either before or after some or all of the hydroxyl protecting groups ($R^3$, $R^4$, $R^5$, $R^8$, and $R^9$) have be removed. In one of the examples illustrated in Scheme 2, all of the hydroxy protecting groups are first removed to form an unprotected N-acetylglucosaminyl-N-acetylmuramic acid (Compound 7) which is then coupled with an alanylisoglutamine derivative to form a glucosaminylmuramyl dipeptide. Alternatively, the $R^2$ protecting group may be selectively removed from a protected glucosaminylmuramic acid ester such as Compound 1 and the resulting muramic acid derivative (Compound 8) coupled with a peptide to produce an O-protected glucosaminylmuramyl dipeptide derivative (Compound 10). Depending on the desired final product, the O-protected glucosaminylmuramyl dipeptide derivative may be subjected to further synthetic transformation or the hydroxy protecting groups may simply be cleaved off to form an unprotected glucosaminylmuramyl dipeptide (e.g., Compound 11).

Depending on the choice of protecting groups, the amino protecting groups of Compound I may often be selectively removed without cleaving the hydroxy or carboxylic protecting groups. If desired, one or more of the amino protecting groups ($Y_1$ and $Y_2$) may also be cleaved and the amine reacted with a different protecting agent prior to carrying out the peptide coupling reaction. For example, the N-phthaloyl portion of a phthalimido group may be removed by butylamine and, if desired, the resulting liberated amino group may be acylated, such as by reaction with acetic anhydride to form an acetyl group (—NHC(O)Me).

Compound IV

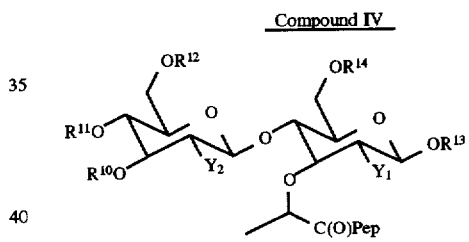

The hydroxyl ($R^3$, $R^4$, $R^5$, $R^8$, and $R^9$) and carboxylic acid ($R^2$) protecting group may be removed by standard techniques such as hydrolysis or hydrogenolysis with hydrogen in the presence of a transition metal catalyst such as palladium. If $R^2$ is removable by reaction with a reducing agent, e.g., by hydrogenolysis where $R^2$ is benzyl or substituted benzyl, a suitable procedure for preparation of the disaccharide peptide (Compound IV) includes the removal of $R^2$ and all of the other benzyl protecting groups followed by the coupling of the resulting disaccharide with a peptide using a coupling agent. The coupling reaction may be carried out using a coupling agent such as N-ethyl-5-phenylisoxazolium-3'-sulphonate ("Woodward's Reagent K") or a carbodiimide (e.g., 1-ethyl-3-(3-dimethylaminopropyl) carbodiimide hydrochloride, "EDCI").

The ester group ($R^2$) may also be selectively removable. This permits the formation of a disaccharide peptide by selective cleavage of the $R^2$ group and coupling of the resulting hydroxy protected disaccharide acid to a peptide using a coupling agent. For example, O-benzylated glucosaminylmuramic acid methyl ester may be treated with a dilute hydroxide solution and the resulting O-benzylated muramic acid derivative may be coupled with the N-terminal amino group of an amino acid or peptide derivative. The coupling reaction may be carried out in the presence of a coupling agent such as 1-ethyl-3-(3-dimethylaminopropyl) carbodiimide hydrochloride in the presence of N-hydroxysuccinimide (SuOH). If desired, the hydroxyl protecting groups may be removed from the resulting disaccharide peptide derivative under standard conditions.

The present invention is further illustrated by way of the following non-limiting examples:

EXAMPLE 1
Preparation of Phenyl 3,4,6-tri-O-acetyl-2-deoxy-2-phthalimido-1-thio-β-D-glucopyranoside (A) A solution of 1,3,4,6-tetra-O-acetyl-2-deoxy-2-phthalimido-β-D-glucopyranose [prepared by the process set forth in B. R. Baker et al., J. Org. Chem. 19: 1786–92, 1954] (477 mg, 1.0 mMol) and phenylthiotrimethyl silane (580 μL, 3.04 Mmol) in anhydrous 1,2-dichloroethane (5 ml) were stirred at 0° C. under an atmosphere of argon. Boron-trifluoride etherate (0.50 ml, 4.06 Mmol) was added to the solution over a period of 30 minutes. The resulting solution was allowed to reach room temperature (RT) over 2 hours then stirred at RT for 20 hours with the exclusion of moisture.

The mixture was diluted with ethyl acetate and then extracted with ice-cold aqueous sodium bicarbonate, washed with water and dried over sodium sulfate. After removing the solvents on a rotary evaporator, the syrupy residue was purifed on a silica gel column using 1:1 ethyl ether-hexane as eluant to yield 410 mg (77.8%) of phenyl 3,4,6-tri-O-acetyl-2-deoxy-2-phthalimido-1-thio-β-D-glucopyranoside as an anomerically homogeneous white solid (mp. 142.5°–143° C.).

The NMR spectra (in $CDCl_3$) were in accord with the desired structure. $^1$H-NMR: δ5.804 (t, 1H, J9.53 Hz, $H_3$); 5.723 (d, 1H, J10.26 Hz, $H_1$); 5.147 (t, 1H, J9.53 Hz, $H_4$) 4.358 (t, 1H, J10.3 Hz, $H_2$); 4.298 (dd, 1H, J11.73 and 5.13 Hz, $H_{6a}$); 4.211 (dd, 1H, J11.73 and 2.20 Hz, $H_{6b}$); 3.910 (ddd, 1H, J10.26, and 5.13 Hz, $H_5$); 7.74–7.89 (m, 4H); 7.25–7.44 (m, 5H). $^{13}$C-NMR: δ170.55, 170.02, 169.38 (3 $COCH_3$); 131.5, 130.9 (2 C=O); 134.4, 134.3, 133.2, 130.9, 128.8, 128.3, 123.6 (aromatic carbons); 83.00 ($C_1$); 75.84 ($C_5$); 71.56 ($C_3$); 68.65 ($C_4$); 62.15 ($C_6$); 53.51 ($C_2$); 20.56, 20.69, 20.34 (3 $CH_3CO$).

(B) 3.82 g (0.008 Mol) of 1,3,4,6-tetra-O-acetyl-2-deoxy-2-phthalimido-β-D-glucopyranose was dissolved in 80 ml of anhydrous dichloromethane and stirred at 0° C. under an atmosphere of nitrogen. To this solution, 4.0 ml (0.032 Mol) of boron trifluoride diethyl etherate was slowly added. This was followed by 2.2 ml (0.021 Mol) of thiophenol. The resulting solution was stirred at 0° C. for 4 hr. and at RT for 2 hr. and then poured into a mixture of ethyl acetate (500 ml) and ice-cold saturated sodium bicarbonate solution (200 ml).

After stirring for 20 minutes, the acetate solution was separated from the aqueous layer, washed successively with more aqueous sodium bicarbonate and water (2×150 ml), dried over sodium sulfate and evaporated to dryness. The residue was crystallized from ether to yield 1.2 g of the product.

The mother liquor was concentrated and then applied to a silica gel column eluted with 1:1 ethyl ether-hexane and to obtain additional phenyl 3,4,6-tri-O-acetyl-2-deoxy-2-phthalimido-β-D-glucopyranoside (1.4 g).

The total yield was 2.6 g (61%). This product was indistinguishable from that obtained in (A).

EXAMPLE 2
Preparation of Benzyl 2-Acetamido-4,6-O-benzylidene-2-deoxy-3-O-[(R)-1-(benzyloxycarbonyl)ethyl]-α-D-glucopyranoside Benzyl 2-acetamido-4,6,-O-dibenzylidene-2-deoxy-3-O-[(R)-1-carboxyethyl]-α-D-glucopyranoside (0.806 g, 1.71 mMol; prepared by the process set forth in Gross et al., Liebigs Ann. Chem., 37–45 (1986)), benzyl alcohol (220 mg, 2.03 mMol), and 4-dimethylaminopyridine (DMAP) (113 mg, 0.925 mMol) was dissolved in 20 ml of anhydrous dichloromethane and 0.5 ml of anhydrous dimethylformamide (DMF). This solution was cooled in an ice-water bath. 1-Ethyl-3-(3-dimethylaminopropyl)carbodiimide hydrochloride (EDCI) (403 mg, 2.06 mMol) was added and the solution was stirred at 0°–5° C. for 2 hours and then at RT for 16 hours.

The solvents were removed in a rotary evaporator, and the residue was then extracted with 80 ml of ethyl acetate and 40 ml of water. The aqueous layer was separated from the organic layer and extracted with 40 ml of ethyl acetate. The combined ethyl acetate solutions were washed with saturated aqueous sodium bicarbonate (2×50 ml) and water (2×50 ml) and then dried over magnesium sulfate. After removing the solvent, the resulting solid residue was recrystallized from ethyl acetate-hexane to yield 0.862 g (89.8%) of benzyl 2-acetamido-4,6-O-benzylidene-2-deoxy-3-O-[(R)-1-(benzyloxycarbonyl)ethyl]-α-D-glucopyranoside as a white amorphous solid (mp. 174.5°–176° C.).

The NMR spectra (in $CDCl_3$) were in accord with the desired structure. $^1$H-NMR: δ5.567 (S, 1H, $CH_2$ph); 5.392 (d, 1H, J2.93 Hz, $H_1$); 5.236, 5.078 (dd, 2H, J12.4 Hz, $COOCH_2$ph); 4.69, 4.52 (dd, 2H, J11.9 Hz, 1-O-$CH_2$pH); 4.569 (q, 1H, J6.96 Hz, MeCH); 1.419 (d, 3H, J6.96 Hz, $CH_3CH$). $^{13}$C-NMR: δ174.78, 170.83, (2C=O); 137.44, 137.16, 135.01 (3 aromatic quaternary carbons); 101.26 ($CH_2$pH); 97.23 ($C_1$).

EXAMPLE 3
Preparation of Benzyl 2-Acetamido-6-O-benzyl-2-deoxy-3-O-[(R)-1-(benzyloxycarbonyl)ethyl]-α-D-glucopyranoside In a 100 ml round bottom flask with three necks was placed 525 mg (0.935 mMol) of benzyl 2-acetamido-4,6-O-benzylidene-2-deoxy-3-O-[(R)-1-(benzyloxycarbonyl) ethyl]-α-D-glucopyranoside, 0.590 g (9.35 mMol) of sodium cyanoborohydride, 12 ml of anhydrous tetrahydrofuran (THF) and 1.5 g of 4 Å molecular sieves. The mixture was stirred at 0° C. for 30 minutes under an atmosphere of argon. 10.5 ml of 1N hydrogen chloride in diethyl ether was added dropwise over a period of 20 minutes and stirring was continued at 0° C. until thin layer chromatography (TLC) (in 39:9:2 chloroform-hexane-iso-propanol) showed the reaction complete (about 2.5 hr.).

Dichloromethane (50 ml) was then added to the reaction mixture and the resulting solution was filtered through celite, then poured into ice-cold 5% sodium bicarbonate solution (25 ml). After stirring for 15 minutes, the aqueous phase was extracted with dichloromethane (2×30 ml). The combined extracts were washed with 5% aqueous sodium bicarbonate (30 ml), and water (2×50 ml); then dried with $MgSO_4$, filtered and concentrated. The oil residue (0.8 g) was applied to a 2.0×32 cm column of silica gel and was eluted with: (A) 200 ml of 1:1 ethyl acetate-hexane, (B) 200 ml of 3:2 ethyl acetate-hexane, (C) 200 ml of 2:1 ethyl acetate-hexane. Combination and evaporation of the appropriate fractions ($R_f$=0.47 in 4:1 ethyl acetate-hexane) afforded 448 mg (85%) of benzyl 2-acetamido-6-O-benzyl-2-deoxy-3-O-[(R)-1-(benzyloxycarbonyl)ethyl]-α-D-glucopyranoside as a colorless syrup.

The NMR spectra (in $CDCl_3$) were in accord with the desired structure. $^1$H-NMR: δ6.82 (d, 1H, NH); 5.142 (dd, 2H, J12.36 Hz, $CooCH_2$ph); 4.973 (d, 1H J3.76 Hz, $H_1$); 4.661 and 4.510 (dd, 2H, J11.82 Hz, 1-O-$CH_2$ph); 4.561 and 4.516 (dd, 2H, J11.82 H, 6-O-CH$_2$ph); 4.359 (q, 1H, J6.98 Hz, CHMe); 4.0102 (ddd, 1H, H$_{6a}$); 1.802 (S, 3H, OAc); 1.448 (d, 3H, J6.98 Hz; CH$_3$CH). $^{13}$C-NMR: 175.37, 172.41 ($^2$C=O); 137.23, 136.75, 134.68 (3 aromatic quaternary carbons); 96.34 (C$_1$); 52.84 (C$_2$); 18.73 (CH$_3$CH); 22.82 (CH$_3$CO); 73.63, 69.70, 69.98, 67.46 (3 CH$_2$ph and C$_6$).

EXAMPLE 4

Preparation of Benzyl 2-acetamido-6-O-benzyl-2-deoxy-3-O-[(R)-1-(methoxycarbonyl)ethyl]-2-D-glucopyranoside (A) In a 100 ml round bottom flask with three necks was placed 529 mg (1.122 mMol) of benzyl 2-acetamido-4,6-O-benzylidene-3-O-[(R)-1-carboxyethyl]-2-deoxy-α-D-glucopyranoside, 15 ml of anhydrous THF, 693 mg (11.02 mMol) of sodium cyanoborohydride, and 2.0 g of 4 Å molecular sieves. The mixture was stirred at 0° C. for 30 minutes under an atmosphere of argon. 11.8 ml of 1N hydrogen chloride in diethyl ether was added dropwise over a period of 40 minutes. The solution was stirred for another 2.5 hr. at 0° C. and then at RT for one additional hour.

After the addition of THF (30 ml), the solution was filtered through celite and the celite was washed with more THF. The combined THF solution was concentrated in a rotary evaporator to leave a yellow oil residue, that was then partitioned between 100 ml of dichloromethane and 50 ml of ice-water and stirred for 15 minutes. The water layer was extracted with dichloromethane (2×25 ml). The organic extracts were combined, washed with 10% sodium chloride solution (3×50 ml), dried over sodium sulfate and evaporated to dryness. The residue (539 mg) was dissolved in 25 ml of methanol and stirred with 2.6 g of silica gel at RT for 2 hr and then allowed to stand overnight. The methanol was removed completely in a rotary evaporator by coevaporation with benzene. The residue was directly loaded onto a column of silica gel (25 g) and eluted with: (A) 50 ml of 2:1 hexane-ethyl ether and (B) chloroform-ether-ethyl acetate (20:9:1). The appropriate fractions were combined and evaporated to yield 348 mg (63.5%) of the product as an amorphous white solid. Recrystallization from ethyl acetate-ether-hexane afforded the desired α-D-glucopyranoside as a crystalline solid (m.p. 116.5°–118° C.). The NMR spectra (in CDCl$_3$) were in accord with the desired structure.
$^1$H-NMR: δ7.489 (d, 1H, NH); 5.192 (d, 1H, J3.1 Hz; H$_1$); 4.503 (q, 1H, J6.96 Hz, CHMe); 4.66 and 4.49 (dd, 2H, J11.8 Hz, 1-O-CH$_2$ph); 4.55 (dd, 2H, J12.4 Hz, 6-O-CH$_2$ph); 3.73 (S, 3H, OCH$_3$); 1.98 (S, 3H, Ac); 1.430 (d, 3H, J6.96 Hz, CH$_3$CH). $^{13}$C-NMR: δ176.09 (COOMe); 171.8 (Ac); 137.13, 137.41 (2 aromatic quaternary carbons); 96.29 (C$_1$); 53.22 (C$_2$); 52.49 (OCH$_3$); 22.89 (Ac); 18.78 (CH$_3$CH).

Also, 96 mg (18.8%) of benzyl 2-acetamido-6-O-benzyl-2-deoxy-3-O-[(R)-1-carboxyethyl]-α-D-glucopyranoside 4,1'-lactone was obtained as an undesired side product.

(B) A solution containing 473 mg (1.003 mMol) of benzyl 2-acetamido-4,6-O-benzylidene-3-O-[(R)-1-carboxyethyl]-2-deoxy-α-D-glucopyranoside, and 174 mg (2.07 mMol) of sodium bicarbonate in 6 ml of anhydrous (DMF) was cooled in an ice bath with stirring. Iodomethane (300 μl; 4.82 mMol) was added to this solution. The mixture was stirred at RT until TLC (in 2:1 ethyl acetate-hexane) indicated the reaction was complete.

The solution was cooled and poured into 50 ml of ice-water with vigorous stirring and then extracted with ethyl acetate. The combined extracts were washed with a sodium chloride solution, dried over sodium sulfate and filtered. After removing the solvent by a rotary evaporator, the solid residue was recrystallized from ethyl acetate-hexane to give 405 mg (83.5%) of benzyl 2-acetamido-4,6-O-benzylidene-3-O-[(R)-1-(methoxycarbonyl)ethyl]-α-D-glucopyranoside (mp. 212.5°–214° C.).

This methyl ester (387 mg, 0.80 mMol) was dissolved in 10 ml of anhydrous THF, mixed with 1.0 g of 4 Å molecular sieves and cooled to 0° C. under an atmosphere of argon. To this solution 525 mg (8.47 mMol) of sodium cyanoborohydride was added, followed by 8.8 ml of 1N hydrogen chloride in diethyl ether. The mixture was stirred at 0° C. for 2 hours and at RT for 1 hour and then diluted with 60 ml of dichloromethane.

After filtration, the dichloromethane solution was stirred with 40 ml of ice-water to which a cold sodium bicarbonate solution was added dropwise to adjust the pH to 5–6. This aqueous solution was separated and extracted with dichloromethane. The combined extracts were washed with 10% brine twice, dried over magnesium sulfate, filtered and concentrated to about 20 ml. 1.9 g of silica gel was added to the solution. The resulting solution was stirred for 5 min. and then evaporated on a rotary evaporator to dryness. The residue was loaded on a column of silica gel (23 g) and eluted with 80 ml hexane followed by 1:1 ethyl acetate-hexane to yield 336 mg (86.5%) of the desired product. It was indistinguishable from that obtained in (A).

EXAMPLE 5

Preparation of Benzyl 2-acetamido-6-O-benzyl-2-deoxy-3-O-[(R)-1-(benzyloxycarbonyl)-β-ethyl]-4-O-(3',4',6'-tri-O-acetyl-2'-deoxy-2'-phthalimido-β-D-glucopyranosyl)-α-D-glucopyranoside Using Nitrosyl Tetrafluoroborate as the Promoter.

In a 50 ml round bottom flask was placed benzyl 2-acetamido-6-O-benzyl-2-deoxy-3-O-[(R)-1-(benzyloxycarbonyl)-ethyl]-α-D-glucopyranoside (257 mg, 0.456 Mmol), methyl 3,4,6-tri-O-acetyl-2-deoxy-2-phthalimido-1-thio-β-D-glucopyranoside (272 mg, 0.583 mMol; prepared by the process set forth in Pozsgay et el., Carbohydr. Res., 179, 61–75 (1988)), anhydrous dichloromethane (5 ml) and powdered 4 Å molecular sieves (1.0 g). The mixture was stirred at 0° C. for 40 minutes under an atmosphere of argon. Nitrosyl tetrafluoroborate (77 mg; 0.66 mMol) was added in portions at 0° C. and the reaction mixture was stirred at 4° C. for 16 hours and at 20° C. for 3 hours with the exclusion of moisture.

Dichloromethane (15 ml) was added at 0° C. followed by 250 μl of triethylamine. The cooled solution was then filtered through celite and evaporated. The oily residue was partitioned between 50 ml of ethyl acetate and 20 ml of water. The water layer was extracted with another 30 ml of ethyl acetate. The combined organic layers were washed with 5% aqueous sodium bicarbonate (2×30 ml) and water (2×40 ml) and then dried over magnesium sulfate. The solvent was evaporated and coevaporated with benzene (2×15 ml) to leave 487 mg of a yellow solid. The yellow solid was then applied to a 1.5×42 cm column of silica gel and eluted with: (A) 120 ml of 2:1 hexane-ethyl acetate; (B) 200 ml of 3:2 hexane-ethyl acetate; (C) 250 ml of 1:1 hexane-ethyl acetate; and (D) 150 ml of 2:3 hexane-ethyl acetate. The appropriate fractions were combined and evaporated to dryness to yield 172 mg (38.4%) of a chromatographically homogeneous white solid (m.p. 134°–6° C., recrystallized from ethyl acetate/ethyl ether/hexane). The NMR spectra (in CDCl$_3$) were in accord with the desired structure.

EXAMPLE 6

Preparation of Benzyl 2-Acetamido-6-O-benzyl-2-deoxy-3-O-[(R)-1-(methoxycarbonyl)ethyl]-4-O-(3',4',6'-tri-O-acetyl-2'-deoxy-2'-phthalimido-β-D-glucopyranosyl)-α-D-glucopyranoside Using N-Bromosuccinimide/Silver Triflate as the Promoter.

A solution of phenyl 3,4,6-tri-O-acetyl-2-deoxy-2-phthalimido-1-thio-β-D-glucopyranoside (217 mg, 0.411 mMol), benzyl 2-acetamido-6-O-benzyl-2-deoxy-3-O-[(R)-1-(methoxycarbonyl)ethyl]-α-D-glucopyranoside (235 mg, 0.482 mMol) and AgOTf (14 mg, 0.05 mMol) in anhydrous dichloromethane (5 ml) was stirred with powdered 4 Å molecular sieves (0.8 g) for 30 minutes under an atmosphere of argon. Recrystallized N-bromosuccinimide (92 mg, 0.516 mMol) was added. The reaction mixture was stirred at 0°–5° C. for 1.5 hr. and at RT for 17 hr. with the exclusion of moisture.

The solution was then diluted with dichloromethane. After filtration through celite, the organic solution (60 ml) was washed successively with 10% sodium bisulfite solution (2×20 ml), water (30 ml), and 10% sodium chloride solution (2×30 ml), and then dried over magnesium sulfate. The solvent was removed on a rotary evaporator and the residue (416 mg) was applied to a 1.5×39 cm column of silica gel. The silica gel was then eluted with 2:1:1 ethyl acetate-diethyl ether-hexane. The appropriate fractions were combined and evaporated to dryness to yield 143 mg (39.0%) of benzyl 2-acetamido-6-O-benzyl-2-deoxy-3-O-[(R)-1-(methoxycarbonyl)ethyl]-4-O-(3',4',6'-tri-O-acetyl-2'-deoxy-2'-phthalimido-β-D-glucopyranosyl)-α-D-glucopyranoside as a chromatographically homogeneous white solid (m.p. 142°–143.5° C., recrystallized from ethyl acetate-ether-hexane). The NMR spectra (in $CDCl_3$) were in accord with the desired structure.

EXAMPLE 7

Preparation of 3,4,6-Tri-O-acetyl-2-deoxy-2-phthalimido-β-D-glucopyranosyl Fluoride Phenyl 3,4,6-tri-O-acetyl-2-deoxy-2-phthalimido-β-D-glucopyranoside (424 mg; 0.805 mMol) was dissolved in 10 ml of anhydrous dichloromethane and cooled to −20° C. under an atmosphere of argon. Diethylaminosulfer trifluoride ("DAST"; 160 µl, 1.21 mMol) was added. The resulting solution was stirred for 5 minutes at −20° C. and then treated with recrystallized N-bromosuccinimide (189 mg; 1.06 mMol). The mixture was stirred at −20° C. to −15° C. for 1 hour and then allowed to react at 0° C. for 1.5 hr.

After adding 50 ml of dichloromethane, the solution was poured into 30 ml of ice-cold 5% sodium bicarbonate solution with stirring. The aqueous solution was separated and extracted with dichloromethane twice. The combined $CH_2Cl_2$ solution was successively washed with a 5% sodium bicarbonate solution and then a 20% brine and water solution. It was then dried over $MgSO_4$ and filtered. After the solvent was removed, the residue was recrystallized from ethyl acetate-hexane to afford 345 mg (98%) of 3,4,6-tri-O-acetyl-2-deoxy-2-phthalimido-β-D-glucopyranosyl fluoride (mp. 116° C.).

The NMR spectrum (in $CDCl_3$) of the β-D-glucopyranosyl fluoride derivative was in accord with the desired structure. $^1$H-NMR: δ6.111 (dd, 1H, $J_{1,2}$ 8.2 Hz $J_{H,F}$ 52.9 Hz, $H_1$); 5.835 (dd, 1H, J9.14 Hz and 10.21 Hz, $H_3$); 5.243 (t, 1H, J9.14 Hz, $H_4$); 4.46 (m, 1H, $H_2$) 4.349 (dd, 1H, J12.36 Hz and 4.8 Hz, H6a) 4.24 (dd, 1H, J12.36 Hz and 2.15 Hz, H6b); 4.00–4.03 (m, 1H, $H_5$); 2.138 (S), 2.052 (S), 1.883 (S) (3 $CH_3$ of Ac). 13C-NMR: δ170.60, 169.99, 169.32 (3 C=0 of Ac); 167.41 (C=0 of phth); 105.29 and 103.12 ($C_1$, $J_{C,F}$ 218 Hz); 54.51 ($C_2$); 20.70, 20.54, 20.34 (3 $CH_3$ of Ac).

EXAMPLE 8

Preparation of Benzyl 2-Acetamido-6-O-benzyl-2-deoxy-3-O-[(R)-1-(methoxycarbonyl)ethyl]-4-O-(3',4',6'-tri-O-acetyl-2'-deoxy-2'-phthalimido-β-D-glucopyranosyl)-α-D-glucopyranoside from the β-D-Glucopyranosyl Fluoride Derivative The β-D-glucopyranosyl fluoride derivative prepared in Example 7 (306 mg; 0.70 mMol) was dissolved in anhydrous dichloromethane (5 ml) and cooled to −15° C.

In a round bottom flask was placed pre-treated $AgClO_4$ (225 mg, 1.06 mMol), $SnCl_2$ (200 mg, 1.05 mMol), 10 ml of anhydrous dichloromethane and 1.0 g of 4 Å powdered molecular sieves. The mixture was stirred at RT for one hour under an atmosphere of argon and then cooled to −20° C.

To this solution was added a second solution of 5 ml anhydrous dichloromethane containing 284 mg (0.588 mMol) of benzyl 2-acetamido-6-O-benzyl-2-deoxy-3-O-[(R)-1-(methoxycarbonyl)-ethyl]-α-D-glucopyranoside. After stirring for 15 minutes at −20° C., the cold solution of the β-D-glucopyranosyl fluoride derivative was added. The reaction mixture was stirred under argon with the exclusion of moisture at −20° C. to −15° C. for 24 hr and then allowed to reach 0° C. over a 2 hour period.

$CH_2Cl_2$ (30 ml) was then added. The resulting solution was filtered through celite, washed with a 5% $NaHCO_3$ solution and a 15% brine and water solution and then dried over $MgSO_4$. After evaporation of the solvent, the residue was applied to a silica gel column and eluted with ethyl acetate-hexane. The appropriate fractions were combined and evaporated to dryness to yield an α-D-glucopyranoside product that was indistinguishable from the product obtained in Example 6.

EXAMPLE 9

Preparation of 2-Acetamido-2-deoxy-β-D-glucopyranosyl-(1→4)-N-acetylmuramic acid A solution containing benzyl 2-acetamido-6-O-benzyl-2-deoxy-3-O-[(R)-1-(benzyloxycarbonyl)ethyl]-4-O-(3',4',6'-tri-O-acetyl-2'-deoxy-2'-phthalimido-β-D-glucopyranosyl)-α-D-glucopyranoside (1.10 g; 1.12 mMol) in methanol (15 ml) was stirred with 2.0 ml of butylamine, refluxed for 4 hours, and then concentrated on a rotary evaporator.

Butylamine was removed by repeated addition of methanol and co-evaporation. The residue was redissolved in 10 ml of methanol and stirred with 1.5 ml of acetic anhydride at 0°–4° C. for 5 hr. After the solvent was removed at RT, the residue was treated with 50 ml of water and lyophilized. The resulting solid was applied to a column of silica gel and eluted with a gradient of methanol/chloroform (from 0% to 4% (V/V) methanol in chloroform). Evaporation of the appropriate fractions gave a chromatographically homogeneous solid, which was dissolved in 50 ml of methanol and 25 ml of acetic acid. After the addition of 5% Pd/C to the resulting solution, the β-D-glucopyranosyl-(1→4)-N-acetylmuramic acid derivative was hydrogenated under hydrogen (35 PSIG) at RT for 24 hours to remove the benzyl protecting groups. The catalyst was removed by filtration through celite and washed with methanol. The filtrate was evaporated to dryness. The resulting solid was recrystallized from methanol-diethyl ether to give 383 mg (68.9%) of N-acetylglucosaminyl-(1→4)-N-acetylmuramic acid (mp. 170°–171.5° C.). The NMR spectra (in $CD_3OD$) were in accord with the desired structure.

EXAMPLE 10

N-Acetyl-β-D-glucosaminyl-(1→4)-N-acetylmuramyl-L-Alanyl-D-iso-Glutamine-benzyl ester N-Acetylglucosaminyl-N-acetylmuramic acid (166 mg; 0.3343 mMol) was dissolved in 6 ml of anhydrous DMF and cooled in an ice-water bath. To this was added 260 µl of a solution containing 133.3 mg/ml of triethylamine in DMF. After 10 minutes, 116 mg (0.435 mMol) of recrystallized Woodward's Reagent K was added and the mixture was stirred for 70 minutes at 0°–2° C. A precooled solution of L-alanyl-D-isoglutamine benzyl ester hydrochloride (120 mg, 0.349 mMol) and triethylamine (TEA) (0.358 mMol) in DMF (5 ml) was added over a period of 15 min at 0° C. The resulting solution was stirred at room temperature for 80 hours. During this time the reaction was followed by TLC (in CHCl$_3$:CH$_3$OH:H$_2$O:NH$_4$OH=50:26:4:2).

When the reaction was complete, DMF was removed in a rotary evaporator at 30° C. The residue was further dried by an oil-pump to give a yellow foam which was dissolved in 7 ml of water, applied to a column (1.5×4 cm) of Dowex® 1×8 (200–400 mesh, acetate form) and eluted with water. The entire eluate (75 ml) was concentrated to about 20 ml and then applied to another column (1.5×21 cm) of Dowex® 50W×8 (100–200 mesh, H$^+$ form) and eluted with 100 ml of water. The collections were combined, concentrated to 50 ml by a rotary evaporator and lyophilized to yield 186 mg (70.9%) of N-acetyl-glucosaminyl-N-acetylmuramyl-L-alanyl-D-isoglutamine benzyl ester as a white solid. The NMR spectrum (in CD$_3$OD) was in accord with the desired structure.

EXAMPLE 11

Preparation of N-Acetyl-β-D-glucosaminyl-(1→4)-N-acetylmuramyl-L-alanyl-D-iso-glutamine (a disaccharide dipeptide derivative of MDP)

In a 250 ml Parr hydrogenation bottle was placed N-acetyl-β-D-glucosaminyl-N-acetylmuramyl-L-alanyl-D-isoglutamine benzyl ester (150 mg, 0.191 mMol), methanol (25 ml), glacial acetic acid (0.5 ml), and 5% Pd/C (67 mg). The mixture was hydrogenated under 30–35 PSIG of hydrogen for 20 hours.

The catalyst was removed by filtration through celite and washed with methanol. The solvents were evaporated in an rotary evaporator below 28° C. and coevaporated with benzene. The solid residue was dissolved in 30 ml of water and lyophilized to give a white fluffy solid in quantitative yield. The NMR spectra (in D$_2$O) were in accord with the desired structure.

The invention has been described with reference to various specific and preferred embodiments and techniques. However, it should be understood that many variations and modifications may be made while remaining within the spirit and scope of the invention.

SCHEME 1

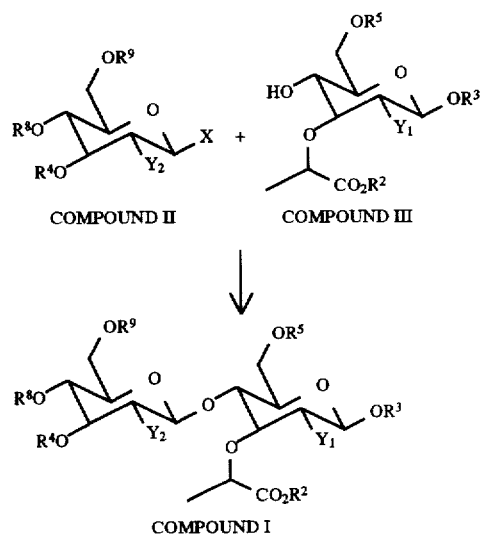

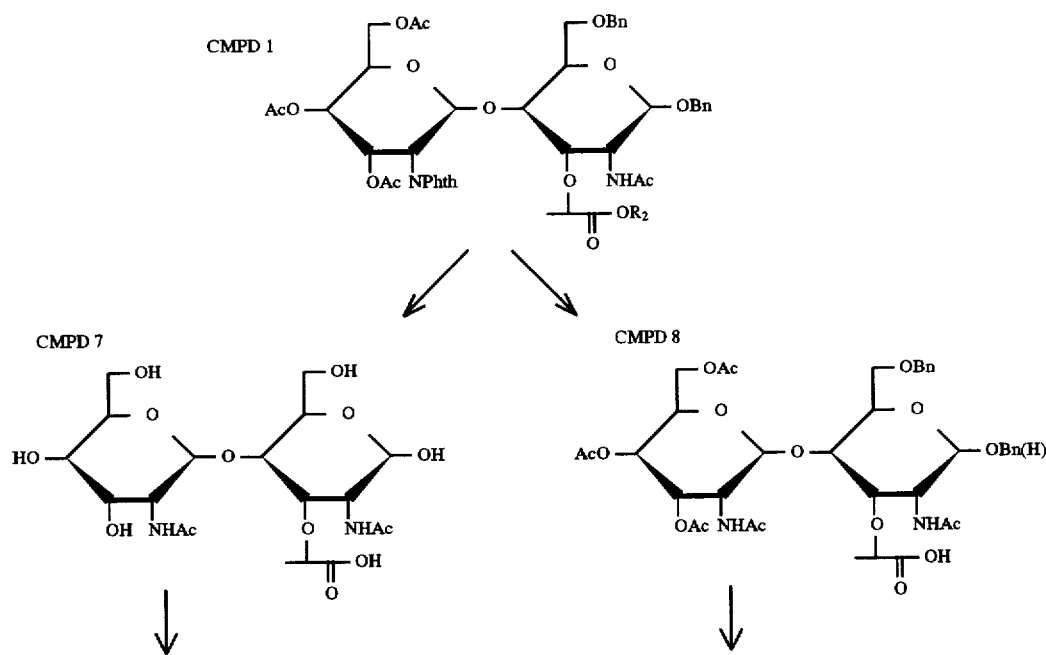

-continued
SCHEME 2

CMPD 9

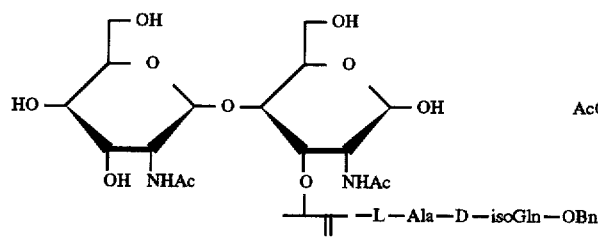

CMPD 10

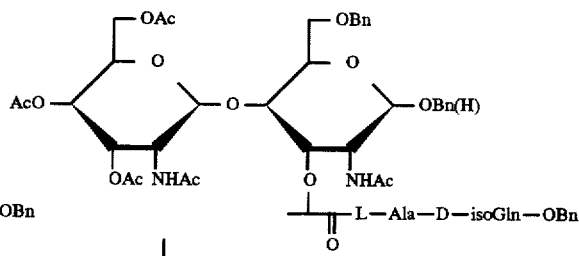

CMPD 11

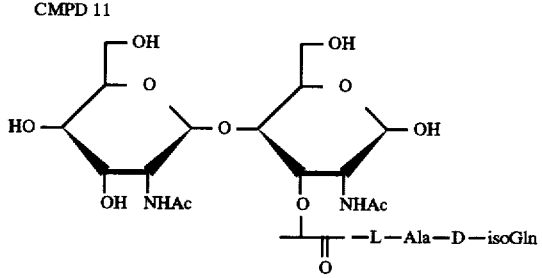

CMPD 11

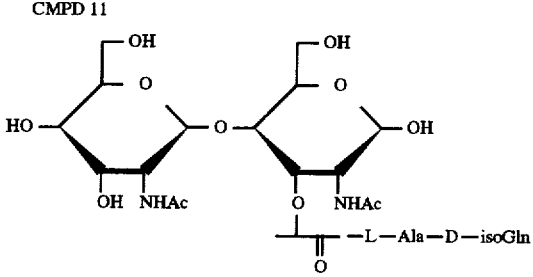

What is claimed is:

1. A muramic acid ester derivative having the formula:

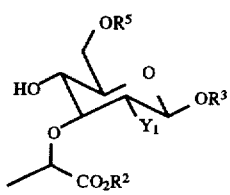

wherein $R^2$ is benzyl or substituted benzyl; $R^3$ and $R^5$ are independently C(1–6)alkyl, substituted C(1–6)alkyl, benzyl, substituted benzyl, or —C(O)R$^6$; and $Y_1$ is NHC(O)R$^{15}$, NHC(O)OR$^7$, phthalimido, maleimido or succinimido;

wherein $R^6$ and $R^{15}$ are independently C(1–6)alkyl, substituted C(1–6)alkyl, benzyl, substituted benzyl, phenyl or substituted phenyl; and $R^7$ is C(1–6)alkyl, substituted C(1–6)alkyl, benzyl, or substituted benzyl.

2. A glucosaminyl muramic acid ester derivative having the formula:

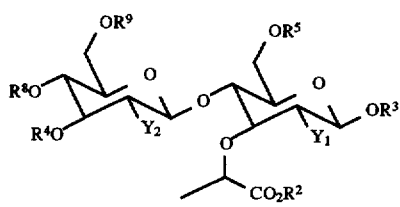

wherein $R^2$ is benzyl or substituted benzyl; $R^3$, $R^4$, $R^5$, $R^8$ and $R^9$ are independently C(1–6)alkyl, substituted C(1–6)alkyl, benzyl, substituted benzyl, or —C(O)R$^6$; $Y_1$ and $Y_2$ are independently NHC(O)R$^{15}$, NHC(O)OR$^7$, phthalimido, maleimido or succinimido;

wherein $R^6$ and $R^{15}$ are independently C(1–6)alkyl, substituted C(1–6)alkyl, benzyl, substituted benzyl, phenyl or substituted phenyl; and $R^7$ is C(1–6)alkyl, substituted C(1–6)alkyl, benzyl, or substituted benzyl.

3. The muramic acid ester derivative of claim 1 wherein $R^2$ is benzyl.

4. The muramic acid ester derivative of claim 1 wherein $R^3$ is benzyl or acetyl; and $R^5$ is benzyl or acetyl.

5. The muramic acid ester derivative of claim 1 wherein $Y_1$ is —NHC(O)Me, phthalimido, maleimido or succinimido.

6. The muramic acid ester derivative of claim 1 wherein $R^2$, $R^3$ and $R^5$ are benzyl; and $Y_1$ is —NHC(O)Me.

7. The glucosaminyl muramic acid ester derivative of claim 2 wherein $Y_1$ and $Y_2$ are independently —NHC(O)Me, phthalimido, maleimido or succinimido.

8. The glucosaminyl muramic acid ester derivative of claim 2 wherein $R^2$ is benzyl.

9. The glucosaminyl muramic acid ester derivative of claim 2 wherein $R^3$, $R^4$, $R^5$, $R^8$ and $R^9$ are independently benzyl or acetyl.

10. The glucosaminyl muramic acid ester derivative of claim 2 wherein $R^2$ is methyl; $R^3$ is benzyl; $R^4$ is acetyl; $R^5$ is benzyl; $R^8$ is acetyl; $R^9$ is acetyl; $Y_1$ is —NHC(O)Me; and $Y_2$ is phthalimido.

* * * * *